United States Patent
Kim et al.

(10) Patent No.: US 12,023,161 B2
(45) Date of Patent: Jul. 2, 2024

(54) DEVICE AND METHOD FOR DETECTING STRESS LEVEL OF DRIVER

(71) Applicants: HYUNDAI MOTOR COMPANY, Seoul (KR); KIA MOTORS CORPORATION, Seoul (KR)

(72) Inventors: Gyun Ha Kim, Incheon (KR); Eung Hwan Kim, Seoul (KR); Sang Kyung Seo, Seoul (KR); Dae Yun An, Anyang (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 315 days.

(21) Appl. No.: 17/071,785

(22) Filed: Oct. 15, 2020

(65) Prior Publication Data

US 2022/0022789 A1 Jan. 27, 2022

(30) Foreign Application Priority Data

Jul. 24, 2020 (KR) ........................ 10-2020-0092458

(51) Int. Cl.
*A61B 5/16* (2006.01)
*A61B 5/00* (2006.01)
*A61B 5/18* (2006.01)
*A61B 5/332* (2021.01)
*B62D 1/04* (2006.01)

(52) U.S. Cl.
CPC ................ *A61B 5/165* (2013.01); *A61B 5/18* (2013.01); *A61B 5/332* (2021.01); *A61B 5/6893* (2013.01); *A61B 5/7221* (2013.01); *B62D 1/04* (2013.01)

(58) Field of Classification Search
CPC ........... A61B 5/165; A61B 5/332; A61B 5/18; A61B 5/6893; A61B 5/7221; B62D 1/04
See application file for complete search history.

(56) References Cited

U.S. PATENT DOCUMENTS

| | | | |
|---|---|---|---|
| 2010/0311482 A1* | 12/2010 | Lange ...................... | A61B 5/35 340/5.82 |
| 2016/0360977 A1* | 12/2016 | Salehizadeh ......... | A61B 5/7253 |
| 2017/0143265 A1* | 5/2017 | Hallberg ............... | A61B 5/7221 |
| 2019/0082993 A1* | 3/2019 | Choi .................... | A61B 5/282 |
| 2020/0022602 A1* | 1/2020 | Park ..................... | A61B 5/7232 |
| 2021/0085201 A1* | 3/2021 | Saitoh ................... | A61B 5/332 |

* cited by examiner

*Primary Examiner* — Linda C Dvorak
*Assistant Examiner* — Abigail Bock
(74) *Attorney, Agent, or Firm* — MORGAN, LEWIS & BOCKIUS LLP

(57) ABSTRACT

A device and a method for detecting a stress level of a driver are provided. The device includes an electrocardiogram sensor for measuring an electrocardiogram of the driver using electrodes arranged on a steering wheel of a vehicle, and a controller that monitors the electrocardiogram of the driver, determines an invalid section in the electrocardiogram based on a shape of the electrocardiogram, and compensates for an electrocardiogram in the determined invalid section.

14 Claims, 6 Drawing Sheets

DEVICE AND METHOD FOR DETECTING STRESS LEVEL OF DRIVER

CROSS-REFERENCE TO RELATED APPLICATION

This application claims priority to and the benefit of Korean Patent Application No. 10-2020-0092458, filed on Jul. 24, 2020, the entire contents of which are incorporated herein by reference.

TECHNICAL FIELD

The present disclosure relates to a technology of detecting a stress level based on an electrocardiogram (ECG) of a vehicle driver.

BACKGROUND

In general, in a scheme of detecting a stress level of a vehicle driver, electrodes may be respectively arranged on left and right sides of a steering wheel of the vehicle, a microcurrent (e.g., an action current resulted from contraction of the heart) flowing through a body of the driver may be obtained through the electrodes, the obtained microcurrent may be filtered to measure an electrocardiogram of the driver, a standard deviation of Normal to Normal (NN) interval (SDNN), which is an analysis index capable of quantifying stress, may be calculated based on the measured electrocardiogram, and it may be determined that the lower the calculated SDNN is, the higher the stress level is, and the higher the calculated SDNN, the lower the stress level is.

An electrocardiogram (hereinafter, an effective electrocardiogram) normally measured for a reference time (e.g., between 30 seconds and 5 minutes) is required to detect the stress level of the vehicle driver as described above. However, for example, in the electrocardiogram measurement process, when the driver temporarily releases a hand from the electrode, when noise resulted from various electronic devices in the vehicle occurs, or when noise resulted from vibration of the vehicle occurs, an electrocardiogram containing an abnormal section (hereinafter, an invalid section) may be measured. In this connection, the invalid section may include a section in which no electrocardiogram signal (action current) is input but only a noise signal is input, or a section in which the electrocardiogram signal is input but is not able to be read because of the noise signal.

A conventional technology of detecting the stress level of the vehicle driver stops (fails) the detection of the stress level when the effective electrocardiogram is not measured, or detects the stress level of the vehicle driver based on the electrocardiogram containing the invalid section.

Therefore, the conventional technology fails to detect the stress level of the vehicle driver whenever the effective electrocardiogram is not measured, thereby causing inconvenience to the vehicle driver. Further, the conventional technology is not able to detect the stress level of the vehicle driver with high accuracy when detecting the stress level of the vehicle driver based on the electrocardiogram containing the invalid section.

The matters described in this background art part are written to improve the understanding of the background of the invention, and may include matters other than the prior art already known to those skilled in the art to which this technology belongs.

SUMMARY

An aspect of the present disclosure provides a device and a method for detecting a stress level of a driver that, in detecting the stress level of the vehicle driver based on an electrocardiogram of the vehicle driver, monitor the electrocardiogram of the vehicle driver, determine an invalid section in the electrocardiogram based on a shape of the electrocardiogram, and compensate for an electrocardiogram in the determined invalid section, thereby minimizing the number of failures in the detection of the stress level of the vehicle driver, and improving an accuracy of the detection of the stress level of the vehicle driver.

The technical problems to be solved by the present inventive concept are not limited to the aforementioned problems, and any other technical problems not mentioned herein will be clearly understood from the following description by those skilled in the art to which the present disclosure pertains.

According to an aspect of the present disclosure, a device for detecting a stress level of a driver includes an electrocardiogram sensor for measuring an electrocardiogram of the driver using electrodes arranged on a steering wheel of a vehicle, and a controller that monitors the electrocardiogram of the driver, determines an invalid section in the electrocardiogram based on a shape of the electrocardiogram, and compensate for an electrocardiogram in the determined invalid section.

In one implementation, the controller may further measure the electrocardiogram of the driver for a time corresponding to the invalid section to compensate for the electrocardiogram in the invalid section.

In one implementation, the controller may compensate for the electrocardiogram in the invalid section by replacing the electrocardiogram in the invalid section with an electrocardiogram measured immediately before the invalid section.

In one implementation, the controller may perform the compensation when the time corresponding to the invalid section is within a critical time.

In one implementation, the controller may terminate the detection of the stress level of the driver when the time corresponding to the invalid section is greater than a critical time.

In one implementation, the controller may reset the measurement of the electrocardiogram when the number of times the invalid section within a critical time has occurred exceeds a reference number of times.

In one implementation, the controller may extend a critical time when the electrocardiogram of the driver is not measured or when hands off of the driver is sensed in a state where the time corresponding to the invalid section is limited to the critical time.

In one implementation, the controller may stop the measurement of the electrocardiogram when a steering angle of the steering wheel of the vehicle exceeds a reference angle, when a speed of the vehicle exceeds a reference speed, when a condition of a surface of a traveling road of the vehicle is an unpaved road, or when the number of road humps consecutively located ahead of the vehicle on the traveling road of the vehicle exceeds a reference number.

According to another aspect of the present disclosure, a method for detecting a stress level of a driver includes measuring, by an electrocardiogram sensor, an electrocardiogram of the driver using electrodes arranged on a steering wheel of a vehicle, monitoring, by a controller, the electrocardiogram of the driver, determining, by the controller, an invalid section in the electrocardiogram based on a shape of the electrocardiogram, and compensating, by the controller, for an electrocardiogram in the determined invalid section.

In one implementation, the compensating for the electrocardiogram in the determined invalid section may include a first compensation operation of further measuring the electrocardiogram of the driver for a time corresponding to the invalid section to compensate for the electrocardiogram in the invalid section.

In one implementation, the compensating for the electrocardiogram in the determined invalid section may include a second compensation operation of compensating for the electrocardiogram in the invalid section by replacing the electrocardiogram in the invalid section with an electrocardiogram measured immediately before the invalid section.

In one implementation, the second compensation operation may include performing the compensation when the time corresponding to the invalid section is within a critical time, terminating the detection of the stress level of the driver when the time corresponding to the invalid section is greater than the critical time, and resetting the measurement of the electrocardiogram when the number of times the invalid section within the critical time has occurred exceeds a reference number of times.

In one implementation, the second compensation operation may further include extending the critical time when vehicle manipulation of the driver is sensed, and stopping the measurement of the electrocardiogram when a steering angle of the steering wheel of the vehicle exceeds a reference angle, when a speed of the vehicle exceeds a reference speed, when a condition of a surface of a traveling road of the vehicle is an unpaved road, or when the number of road humps consecutively located ahead of the vehicle on the traveling road of the vehicle exceeds a reference number.

DRAWINGS

In order that the disclosure may be well understood, there will now be described various forms thereof, given by way of example, reference being made to the accompanying drawings, in which.

DETAILED DESCRIPTION

Figure 1:
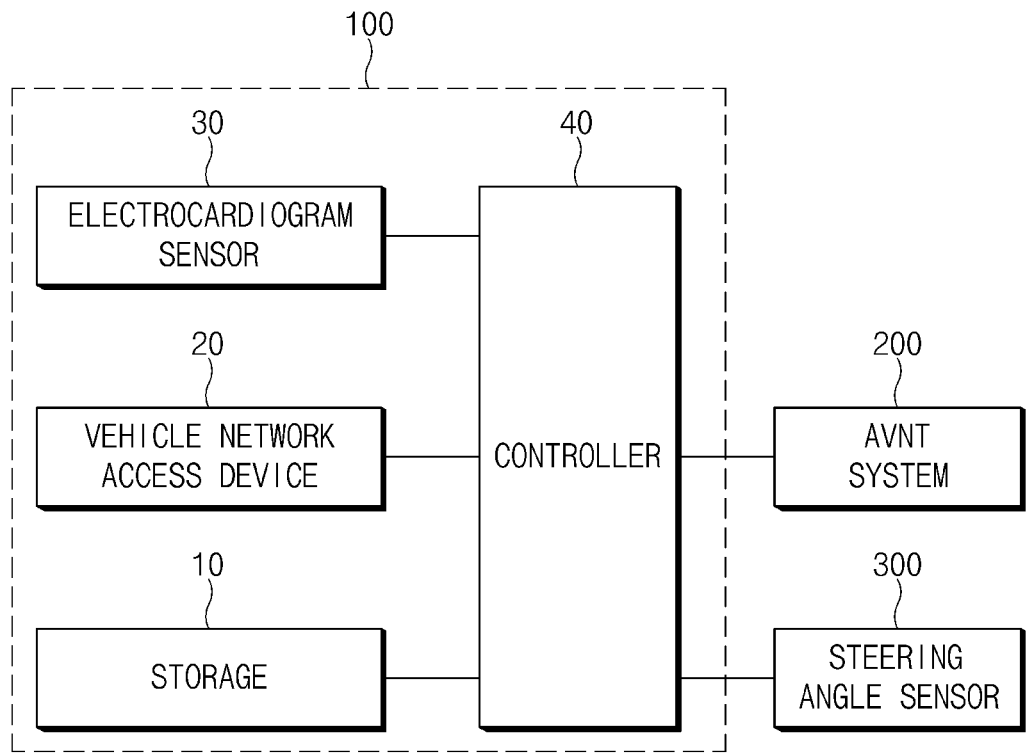
FIG. 1 is a configuration diagram of a driver's stress level detecting device in one form of the present disclosure.

Hereinafter, some embodiments of the present disclosure will be described in detail with reference to the exemplary drawings. In adding the reference numerals to the components of each drawing, it should be noted that the identical or equivalent component is designated by the identical numeral even when they are displayed on other drawings. Further, in describing the embodiment of the present disclosure, a detailed description of the related known configuration or function will be omitted when it is determined that it interferes with the understanding of the embodiment of the present disclosure.

In describing the components of the embodiment according to the present disclosure, terms such as first, second, A, B, (a), (b), and the like may be used. These terms are merely intended to distinguish the components from other components, and the tams do not limit the nature, order or sequence of the components. Unless otherwise defined, all terms including technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a configuration diagram of a driver's stress level detecting device according to an embodiment of the present disclosure.

As shown in FIG. 1, a driver's stress level detecting device 100 according to an embodiment of the present disclosure may include storage 10, a vehicle network access device 20, an electrocardiogram sensor 30, and a controller 40. In this connection, components may be coupled with each other to be implemented as a single component or some components may be omitted based on a scheme of implementing the driver's stress level detecting device 100 according to an embodiment of the present disclosure.

In a description of each of the components, first, the storage 10 may store various logics, algorithms, and programs required in a process of monitoring the electrocardiogram of the vehicle driver, determining an invalid section in the electrocardiogram based on a shape of the electrocardiogram, and compensating for an electrocardiogram in the determined invalid section in detecting a stress level of a vehicle driver based on an electrocardiogram of the vehicle driver. In this connection, the invalid section may include a section in which no electrocardiogram signal (action current) is input and only a noise signal is input or a section in which the electrocardiogram signal is input but is not able to be read because of the noise signal (a section in which the shape of the electrocardiogram does not appear). Such invalid section may be, for example, a section β shown in FIG. 2B.

Figure 2A:
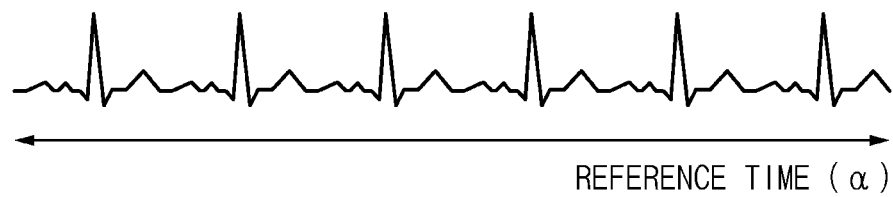
FIG. 2A is an exemplary diagram of a normal electrocardiogram measured by an electrocardiogram sensor disposed in a driver's stress level detecting device in one form of the present disclosure.

The storage 10 may store a measurement time (hereinafter, a reference time) of an effective electrocardiogram used to detect the stress level of the vehicle driver. In this connection, the effective electrocardiogram means an electrocardiogram measured without the invalid section for the reference time. Such effective electrocardiogram is, for example, as shown in FIG. 2A. In addition, a reference time α may be, for example, a value in a range from 30 seconds to 5 minutes.

The storage 10 may store a critical time (e.g., 5 seconds) for limiting a length of the invalid section in the electrocardiogram.

In the process of detecting the stress level of the vehicle driver, when the vehicle driver performs manipulations on various functions of the vehicle, the storage 10 may further store an additional time (e.g., 2 seconds) for extending the critical time.

The storage 10 may include a storage medium of at least one type of memory such as a flash memory type, a hard disk type, a micro type, and a card type (for example, a secure digital card (SD card) or an extream digital card (XD card)), and the like, and a memory such as a random access memory (RAM), a static RAM (SRAM), a read only memory (ROM), a programmable ROM (PROM), an electrically erasable PROM (EEPROM), a magnetic RAM (MRAM), a magnetic disk, and an optical disk.

The vehicle network access device 20, which is a module that provides an interface of access to a vehicle network, may obtain various vehicle information, travel information, driving information, manipulation information, and the like from the vehicle network under control of the controller 40.

As an example, the vehicle network access device 20 may obtain, as the vehicle manipulation information, steering wheel remote controller (SWRC) switch manipulation information (manipulation signal), transmission manipulation information, air conditioning switch manipulation information, in-vehicle switch manipulation information, and the like. In this connection, the in-vehicle switch manipulation information may include window switch manipulation information, sunroof switch manipulation information, multi-function switch manipulation information, lamp switch manipulation information, seat adjusting switch manipulation information, and the like.

Such vehicle network may include a controller area network (CAN), a controller area network with flexible data-rate (CAN FD), a local interconnect network (LIN), a FlexRay, a media oriented system transport (MOST), an Ethernet, and the like.

Figure 3:
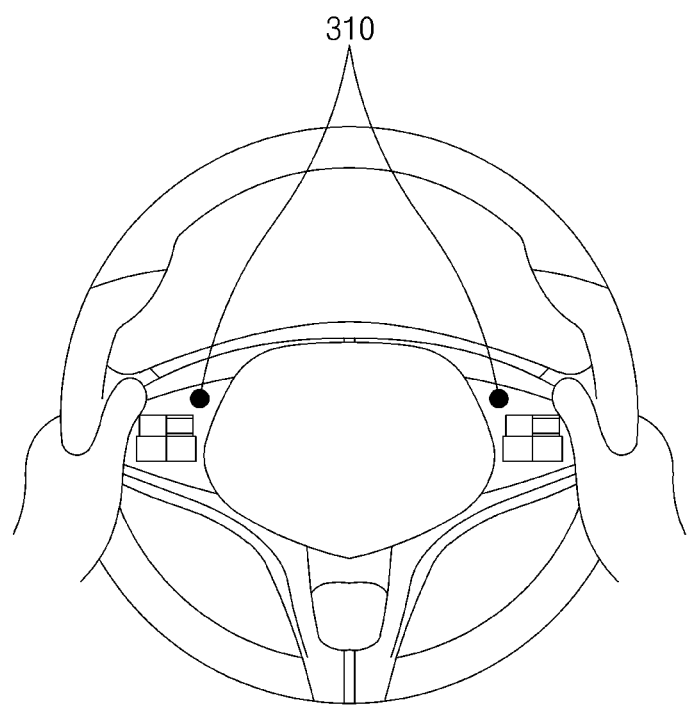
FIG. 3 is an exemplary view of an installation position of an electrode in an electrocardiogram sensor disposed in a driver's stress level detecting device in one form of the present disclosure.

The electrocardiogram sensor 30 may be equipped with electrodes 310 respectively on left and right sides of a steering wheel of the vehicle as shown in FIG. 3. The electrocardiogram sensor 30 may obtain a microcurrent (e.g., an action current resulted from contraction of the heart) flowing through a body of the driver through the electrodes 310, and measure the electrocardiogram of the driver based on the obtained microcurrent. As an example, a normal electrocardiogram is as shown in FIG. 2A.

The controller 40 pertains overall control such that each of the components may normally perform a function thereof. Such controller 40 may be implemented in a form of hardware, may be implemented in a form of software, or may be implemented in a form in which the hardware and the software are combined with each other. Preferably, the controller 40 may be implemented as a microprocessor, but may not be limited thereto.

In particular, in detecting the stress level of the vehicle driver based on the electrocardiogram of the vehicle driver, the controller 40 may perform various controls in the process of monitoring the electrocardiogram of the vehicle driver, determining the invalid section in the electrocardiogram based on the shape of the electrocardiogram, and compensating for the electrocardiogram in the determined invalid section.

The controller 40 may read various information stored in the storage 10.

The controller 40 may access the vehicle network through the vehicle network access device 20 to obtain various information.

The controller 40 may control the electrocardiogram sensor 30 to measure the electrocardiogram of the vehicle driver.

The controller 40 may collect, from an audio video navigation telematics (AUNT) system 200 disposed in vehicle, information (e.g., a road shape, a road curvature, a lane, a road type, and the like) on a road on which the vehicle is currently traveling, route information (left turn, right turn, U-turn, and the like), road surface information (asphalt, unpaved, a gravel road, and the like), road hump information, accident information, speed information, and the like.

The controller 40 may obtain audio manipulation information, video manipulation information, navigation manipulation information, telematics manipulation information, and the like of the vehicle driver in connection with the AUNT system 200 disposed in the vehicle.

The controller 40 may obtain steering angle information of the steering wheel through a steering angle sensor 300 disposed in the vehicle.

Hereinafter, an operation of the controller 40 will be described in detail with reference to FIGS. 2A to 2D.

Figure 2B:
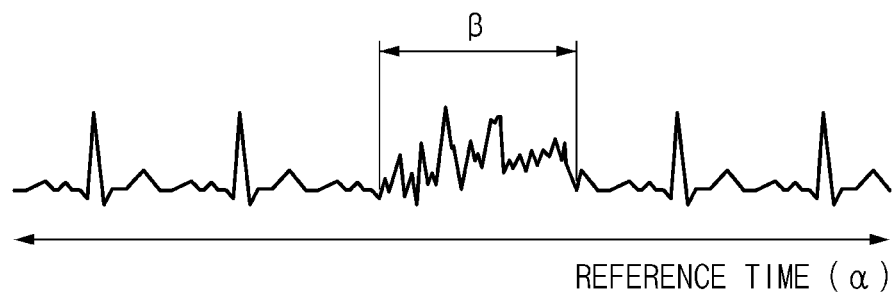
FIG. 2B is an exemplary diagram of an electrocardiogram containing an invalid section measured by an electrocardiogram sensor disposed in a driver's stress level detecting device in one form of the present disclosure.
Figure 2C:
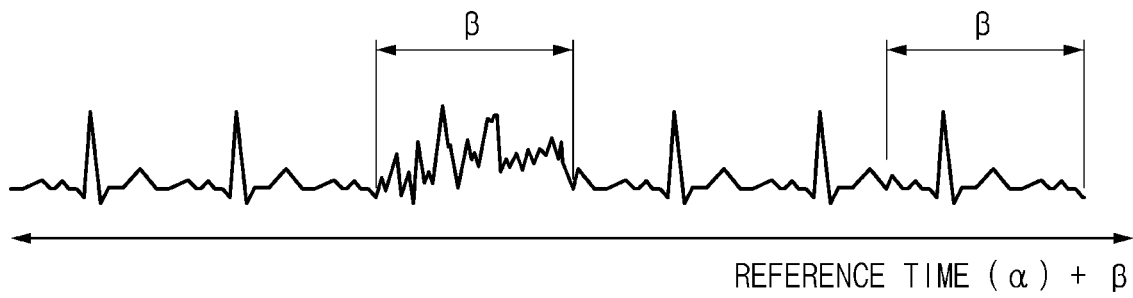
FIG. 2C is an exemplary diagram showing a result of compensating for an electrocardiogram in an invalid section by a controller disposed in a driver's stress level detecting device in one form of the present disclosure.
Figure 2D:
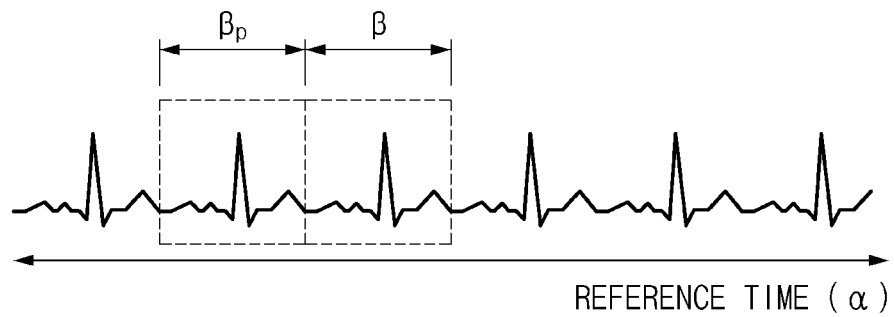
FIG. 2D is another exemplary view showing a result of compensating for an electrocardiogram in an invalid section by a controller disposed in a driver's stress level detecting device in one form of the present disclosure.

FIG. 2A is an exemplary diagram of a normal electrocardiogram measured by an electrocardiogram sensor disposed in a driver's stress level detecting device according to an embodiment of the present disclosure. FIG. 2B is an exemplary diagram of an electrocardiogram containing an invalid section measured by an electrocardiogram sensor disposed in a driver's stress level detecting device according to an embodiment of the present disclosure. FIG. 2C is an exemplary diagram showing a result of compensating for an electrocardiogram in an invalid section by a controller disposed in a driver's stress level detecting device according to an embodiment of the present disclosure. Further, FIG. 2D is another exemplary view showing a result of compensating for an electrocardiogram in an invalid section by a controller disposed in a driver's stress level detecting device according to an embodiment of the present disclosure.

The controller 40 may monitor whether the normal electrocardiogram measured by the electrocardiogram sensor 30 is measured for the reference time as shown in FIG. 2A. This is because the electrocardiogram normally measured for the reference time is required to specify the stress level of the vehicle driver.

The controller 40 may determine the invalid section based on the shape of the electrocardiogram in the process of monitoring the electrocardiogram measured by the electrocardiogram sensor 30. As an example, the controller 40 may determine a section (the section β) that does not have the shape of the electrocardiogram as the invalid section as shown in FIG. 2B. In this connection, the section β is a time section as may be seen through FIG. 2B.

The controller 40 may compensate for the electrocardiogram in the determined invalid section in following two schemes.

As a first scheme, as shown in FIG. 2C, the controller 40 may additionally measure the electrocardiogram by extending the reference time α by the invalid section β, thereby compensating for the electrocardiogram in the invalid section β.

As a second scheme, as shown in FIG. 2D, the controller 40 may replace the electrocardiogram in the invalid section β with an electrocardiogram measured immediately before, thereby compensating for the electrocardiogram in the invalid section β. That is, the controller 40 may replace the electrocardiogram in the invalid section β with an electrocardiogram in an immediately preceding section $β_P$. In this connection, the length (a time) of the invalid section β and a length (a time) of the immediately preceding section $β_P$ are the same.

In one example, in relation to the two compensation schemes, the controller 40 may limit the time of the invalid section β, and determine whether to compensate for the invalid section β based on the limited time.

As an example, the controller 40 may compensate for the electrocardiogram in the first scheme when the time of the invalid section β is within the critical time (e.g., 5 seconds). In this connection, in the process of measuring the electrocardiogram for the reference time required to detect the stress level of the vehicle driver, when the number of times the invalid section β within the critical time has occurred exceeds the reference number of times (e.g., 2 times), the controller 40 may discard a previously measured electrocardiogram and newly measure an electrocardiogram. That is, the controller 40 may reset the electrocardiogram measurement. In addition, the controller 40 may terminate the detection of the stress level of the vehicle driver when the time of the invalid section β is greater than the critical time (e.g., 5 seconds).

As another example, the controller 40 may compensate for the electrocardiogram in the second scheme when the time of the invalid section β is within a critical time (for example, 5 seconds). In this connection, in the process of measuring the electrocardiogram for the reference time required to detect the stress level of the vehicle driver, when the number of times the invalid section β within the critical time has occurred exceeds the reference number of times (e.g., 2 times), the controller 40 may discard the previously measured electrocardiogram and newly measure the electrocardiogram. That is, the controller 40 may reset the electrocardiogram measurement and initiate a new electrocardiogram measurement. In addition, the controller 40 may terminate the detection of the stress level of the vehicle driver when the time of the invalid section β is greater than the critical time (e.g., 5 seconds).

In a state in which the time of the invalid section β is limited, when the vehicle driver has performed the manipulations on the various functions of the vehicle, the controller 40 may extend the critical time by the additional time (e.g., 2 seconds).

When one of cases in which a steering angle of the steering wheel of the vehicle exceeds a reference angle (e.g., 180°), a vehicle speed exceeds a reference speed (e.g., 150 km/h), a condition of the surface of the road on which the vehicle is traveling is the unpaved road (a dirt road, the gravel road, and the like), and the number of road humps consecutively located ahead of the vehicle (e.g., within 10 m) on the road on which the vehicle is traveling exceeds the reference number is satisfied, the controller 40 may stop the electrocardiogram measurement or may not initiate the electrocardiogram measurement at all.

The controller 40 may specify the stress level of the vehicle driver based on the compensated electrocardiogram. In this connection, a technology of specifying the stress level based on the electrocardiogram is a well-known and common technology, so that any technology may be used.

In one example, the controller 40 may sense hands off of the vehicle driver in various schemes.

As an example, the controller 40 may apply a test current (a current equal to or below 30 μA having a frequency of 500 Hz) to one of the two electrodes, determine that the vehicle driver is in a hands on state when the same test current is sensed from the other electrode, and determine that the vehicle driver is in a hands off state when the same test current is not sensed from the other electrode.

As another example, the controller 40 may determine whether the vehicle driver is in the hands on/hands off state from an image of the vehicle driver captured through an infrared camera or a time of flight (ToF) camera disposed in the vehicle.

As another example, the controller 40 may determine that the vehicle driver is in the hands on state when a steering torque measured by a steering torque sensor disposed in the vehicle is irregular, and determine that the vehicle driver is in the hands off state when the torque is not measured by the steering torque sensor.

As another example, the controller 40 may determine whether the vehicle driver is in the hands on/hands off state based on a change in impedance measured by a capacitance sensor mounted on a steering wheel.

Figure 4:
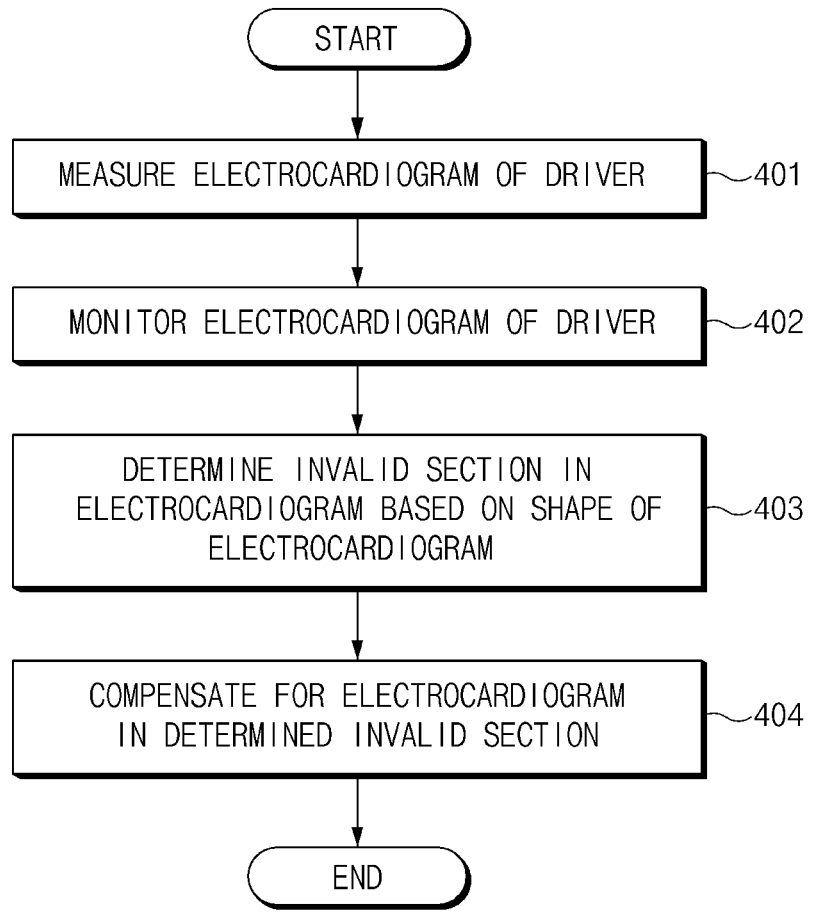
FIG. 4 is a flowchart of a driver's stress level detecting method in one form of the present disclosure.

FIG. 4 is a flowchart of a driver's stress level detecting method according to an embodiment of the present disclosure.

First, the electrocardiogram sensor 30 measures the electrocardiogram of the driver using the electrodes arranged on the steering wheel of the vehicle (401).

Thereafter, the controller 40 monitors the electrocardiogram of the driver (402).

Thereafter, the controller 40 determines the invalid section in the electrocardiogram based on the shape of the electrocardiogram (403).

Thereafter, the controller 40 compensates for the electrocardiogram in the determined invalid section (404).

Figure 5:
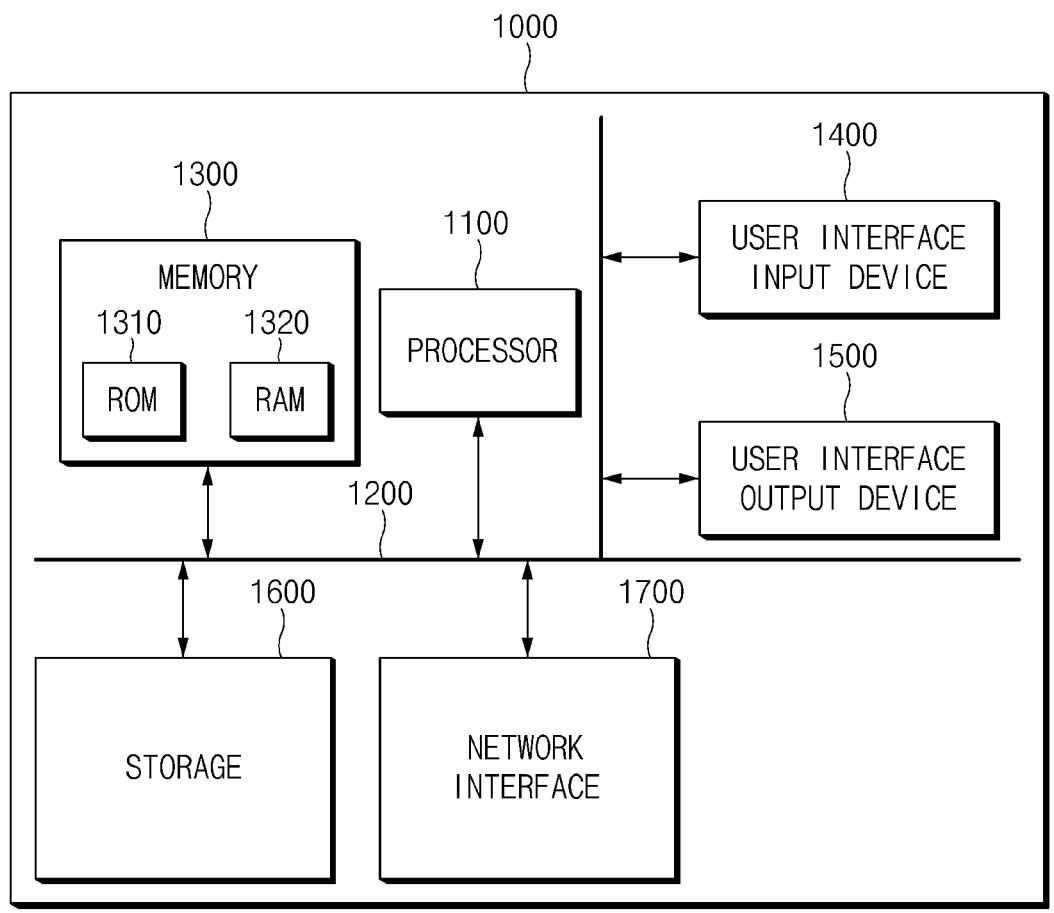
FIG. 5 is a block diagram showing a computing system for executing a driver's stress level detecting method in one form of the present disclosure.

FIG. 5 is a block diagram showing a computing system for executing a driver's stress level detecting method according to an embodiment of the present disclosure.

Referring to FIG. 5, the driver's stress level detecting method according to an embodiment of the present disclosure may also be implemented through a computing system. A computing system 1000 may include at least one processor 1100, a memory 1300, a user interface input device 1400, a user interface output device 1500, storage 1600, and a network interface 1700 connected via a bus 1200.

The processor 1100 may be a central processing unit (CPU) or a semiconductor device that performs processing on commands stored in the memory 1300 and/or the storage 1600. The memory 1300 and the storage 1600 may include various types of volatile or non-volatile storage media. For example, the memory 1300 may include a ROM (Read Only Memory) 1310 and a RAM (Random Access Memory) 1320.

Thus, the operations of the method or the algorithm described in connection with the embodiments disclosed herein may be embodied directly in hardware or a software module executed by the processor 1100, or in a combination thereof. The software module may reside on a storage medium (that is, the memory 1300 and/or the storage 1600) such as a RAM, a flash memory, a ROM, an EPROM, an EEPROM, a register, a hard disk, a solid state drive (SSD), a removable disk, and a CD-ROM. The exemplary storage medium is coupled to the processor 1100, which may read information from, and write information to, the storage medium. In another method, the storage medium may be integral with the processor 1100. The processor and the storage medium may reside within an application specific integrated circuit (ASIC). The ASIC may reside within the user terminal. In another method, the processor and the storage medium may reside as individual components in the user terminal.

The description above is merely illustrative of the technical idea of the present disclosure, and various modifications and changes may be made by those skilled in the art without departing from the essential characteristics of the present disclosure.

Therefore, the embodiments disclosed in the present disclosure are not intended to limit the technical idea of the present disclosure but to illustrate the present disclosure, and the scope of the technical idea of the present disclosure is not limited by the embodiments. The scope of the present disclosure should be construed as being covered by the scope of the appended claims, and all technical ideas falling within the scope of the claims should be construed as being included in the scope of the present disclosure.

The device and the method for detecting the stress level of the driver according to an embodiment of the present disclosure described above may, in detecting the stress level of the vehicle driver based on the electrocardiogram of the vehicle driver, monitor the electrocardiogram of the vehicle driver, determine the invalid section in the electrocardiogram based on the shape of the electrocardiogram, and compensate for the electrocardiogram in the determined invalid section, thereby minimizing the number of failures in the detection of the stress level of the vehicle driver, and improving the accuracy of the detection of the stress level of the vehicle driver.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. A device for detecting a stress level of a driver, the device comprising:
   an electrocardiogram sensor configured to measure an electrocardiogram of the driver using electrodes arranged on a steering wheel of a vehicle; and
   a controller configured to:
      monitor the electrocardiogram of the driver;
      set a time period based on a peak voltage periodically appearing in the electrocardiogram;
      determine the time period in which the peak voltages appear periodically as a valid time period;
      determine a time period in which the peak voltage does not appear periodically as an invalid time period; and
      compensate for an electrocardiogram in the invalid time period,
   wherein the controller is further configured to:
      measure the electrocardiogram of the driver during the valid time period; and
      compensate for the electrocardiogram in the invalid time period by using the measured electrocardiogram during the valid time period, and
   wherein the controller is further configured to perform the compensation when a time period corresponding to the invalid time period is within a critical time period.

2. The device of claim 1, wherein the controller is configured to:
   terminate the detection of the stress level of the driver when the time period corresponding to the invalid time period is greater than the critical time period.

3. The device of claim 1, wherein the controller is configured to:
   reset the measurement of the electrocardiogram when a number of times for the invalid time period within the critical time period exceeds a reference number of times.

4. The device of claim 1, wherein the controller is configured to:
   extend the critical time period when the electrocardiogram of the driver is not measured or when hands-off of the driver is sensed in a state where the time period corresponding to the invalid time period is limited to the critical time period.

5. The device of claim 1, wherein the controller is configured to:
   stop the measurement of the electrocardiogram when a steering angle of the steering wheel of the vehicle exceeds a reference angle, when a speed of the vehicle exceeds a reference speed, when a condition of a surface of a traveling road of the vehicle is an unpaved road, or when a number of road bumps consecutively located ahead of the vehicle on the traveling road exceeds a reference number.

6. A device for detecting a stress level of a driver, the device comprising:
   an electrocardiogram sensor configured to measure an electrocardiogram of the driver using electrodes arranged on a steering wheel of a vehicle; and
   a controller configured to:
      monitor the electrocardiogram of the driver;
      set a time period based on a peak voltage periodically appearing in the electrocardiogram;
      determine the time period in which the peak voltages appear periodically as a valid time period;
      determine a time period in which the peak voltage does not appear periodically as an invalid time period; and
      compensate for an electrocardiogram in the invalid time period,
   wherein the controller is configured to compensate for the electrocardiogram in the invalid time period by replacing the electrocardiogram in the invalid time period with electrocardiogram in the valid time period, and
   wherein the controller is further configured to perform the compensation when a time period corresponding to the invalid time period is within a critical time period.

7. The device of claim 6, wherein the controller is configured to:
   terminate the detection of the stress level of the driver when the time period corresponding to the invalid time period is greater than the critical time period.

8. The device of claim 6, wherein the controller is configured to:
   reset the measurement of the electrocardiogram when a number of times for the invalid time period within the critical time period exceeds a reference number of times.

9. The device of claim 6, wherein the controller is configured to:
   extend the critical time period when the electrocardiogram of the driver is not measured or when hands-off of the driver is sensed in a state where the time period corresponding to the invalid time period is limited to the critical time period.

10. The device of claim 6, wherein the controller is configured to:
    stop the measurement of the electrocardiogram when a steering angle of the steering wheel of the vehicle exceeds a reference angle, when a speed of the vehicle exceeds a reference speed, when a condition of a surface of a traveling road of the vehicle is an unpaved road, or when a number of road bumps consecutively located ahead of the vehicle on the traveling road exceeds a reference number.

11. A method for detecting a stress level of a driver, the method comprising:

monitoring, by a controller, the electrocardiogram of the driver;

setting, by the controller, a time period based on a peak voltage periodically appearing in the electrocardiogram;

determining, by the controller, the time period in which the peak voltages appear periodically as a valid time period;

determining, by the controller, a time period in which the peak voltage does not appear periodically as an invalid time period; and compensating, by the controller, for an electrocardiogram in the invalid time period, wherein the compensating for the electrocardiogram in the invalid time period includes:

measuring the electrocardiogram of the driver during the valid time period compensating for the electrocardiogram in the invalid time period by using the measured electrocardiogram during the valid time period, and wherein the measuring the electrocardiogram of the driver includes:
- performing the compensation when a time period corresponding to the invalid time period is within a critical time period;
- terminating the detection of the stress level of the driver when the time period corresponding to the invalid time period is greater than the critical time period; and
- resetting the measurement of the electrocardiogram when a number of times for the invalid time period within the critical time period exceeds a reference number of times.

12. The method of claim 11, wherein the measuring the electrocardiogram of the driver further includes:
- extending the critical time period when vehicle manipulation of the driver is sensed; and
- stopping the measurement of the electrocardiogram when a steering angle of a steering wheel of the vehicle exceeds a reference angle, when a speed of the vehicle exceeds a reference speed, when a condition of a surface of a traveling road of the vehicle is an unpaved road, or when a number of road bumps consecutively located ahead of the vehicle on the traveling road exceeds a reference number.

13. A method for detecting a stress level of a driver, the method comprising:

monitoring, by a controller, an electrocardiogram of the driver;

setting, by the controller, a time period based on a peak voltage periodically appearing in the electrocardiogram;

determining, by the controller, a time period in which the peak voltages appear periodically as a valid time period;

determining, by the controller, a time period in which the peak voltage does not appear periodically as an invalid time period; and compensating, by the controller, for an electrocardiogram in the invalid time period, wherein the compensating for the electrocardiogram in the invalid time period includes:

compensating for the electrocardiogram in the invalid time period by replacing the electrocardiogram in the invalid time period with the electrocardiogram in the valid time period, and wherein the replacing the electrocardiogram in the invalid time period includes:
- performing the compensation when a time period corresponding to the invalid time period is within a critical time period;
- terminating the detection of the stress level of the driver when the time period corresponding to the invalid time period is greater than the critical time period; and
- resetting the measurement of the electrocardiogram when a number of times for the invalid time period within the predetermined time exceeds a reference number of times.

14. The method of claim 13, wherein the replacing the electrocardiogram in the invalid time period further includes:
- extending the predetermined time period when vehicle manipulation of the driver is sensed; and
- stopping the measurement of the electrocardiogram when a steering angle of the steering wheel of the vehicle exceeds a reference angle, when a speed of the vehicle exceeds a reference speed, when a condition of a surface of a traveling road of the vehicle is an unpaved road, or when a number of road bumps consecutively located ahead of the vehicle on the traveling road exceeds a reference number.

* * * * *